United States Patent
Karram et al.

(10) Patent No.: US 12,193,925 B2
(45) Date of Patent: Jan. 14, 2025

(54) DEVICE FOR TREATING URINARY STRESS INCONTINENCE

(71) Applicants: Mickey M Karram, Cincinnati, OH (US); Dionysios K. Veronikis, St. Louis, MO (US)

(72) Inventors: Mickey M Karram, Cincinnati, OH (US); Dionysios K. Veronikis, St. Louis, MO (US)

( * ) Notice: Subject to any disclaimer, the term of this patent is extended or adjusted under 35 U.S.C. 154(b) by 0 days.

(21) Appl. No.: 17/139,035

(22) Filed: Dec. 31, 2020

(65) Prior Publication Data
US 2022/0202551 A1    Jun. 30, 2022

(51) Int. Cl.
| A61F 2/00 | (2006.01) |
| A61B 17/00 | (2006.01) |
| A61B 17/06 | (2006.01) |
| A61M 29/00 | (2006.01) |

(52) U.S. Cl.
CPC .... *A61F 2/0045* (2013.01); *A61F 2220/0008* (2013.01)

(58) Field of Classification Search
CPC ............ A61F 2/0045; A61F 2220/0008; A61F 2220/0016; A61F 2/0004; A61F 2/0063; A61B 17/0401; A61B 2017/00805
See application file for complete search history.

(56) References Cited

U.S. PATENT DOCUMENTS

| 5,899,909 | A  | * | 5/1999 | Claren | A61B 17/06109 606/118 |
| 7,601,118 | B2 | * | 10/2009 | Smith | A61B 17/06109 600/30 |
| 8,574,149 | B2 | * | 11/2013 | Evans | A61B 17/06109 606/151 |
| 9,282,958 | B2 | * | 3/2016 | Chu | A61F 2/0045 |
| 2001/0018549 | A1 | * | 8/2001 | Scetbon | A61F 2/0045 600/29 |
| 2006/0058578 | A1 | * | 3/2006 | Browning | A61F 2/0045 600/30 |
| 2008/0004490 | A1 | * | 1/2008 | Bosley, Jr. | A61F 2/0045 606/232 |
| 2009/0018387 | A1 | * | 1/2009 | Veronikis | A61F 2/0045 600/37 |
| 2014/0228971 | A1 | * | 8/2014 | Kim | A61L 27/56 623/23.72 |

* cited by examiner

*Primary Examiner* — Thaddeus B Cox
*Assistant Examiner* — Joshua Daryl D Lannu
(74) *Attorney, Agent, or Firm* — Harness, Dickey & Pierce, P.L.C.

(57) ABSTRACT

An implantable device for treating a patient suffering from female urinary stress incontinence includes an elongate sling for supporting the urethra, the sling having first and second ends. First and second tabs extend from the first and second ends of the sling, respectively for engaging supportive tissue superior to the portion of the urethra being supported. Each tab has a ratcheted section of alternating relatively projecting and relatively recessed portions for engaging the supportive tissue.

14 Claims, 4 Drawing Sheets

DEVICE FOR TREATING URINARY STRESS INCONTINENCE

FIELD

The present disclosure relates to devices for the treatment of urinary stress incontinence.

BACKGROUND

This section provides background information related to the present disclosure which is not necessarily prior art.

Urinary stress incontinence in the involuntary loss of urine when physical movement or activity, such as from coughing, sneezing, running, or lifting, applies pressure to the bladder causing it to leak through the urethra. The urethra, when properly supported, normally maintains a tight seal to prevent involuntary loss of urine. However, in a woman suffering from urinary stress incontinence, the surrounding tissue for a variety of reasons, is unable to adequately support the urethra in its correct position. As a result, during normal movements when pressure is exerted on the bladder from the diaphragm, the urethra cannot retain its seal, permitting urine to escape.

Various methods and apparatus have been developed to treat urinary stress incontinence by supporting the urethra in the proper position. Examples of such treatment methods and apparatus include those disclosed in U.S. Pat. Nos. 5,122,344, 5,899,909, 6,932,759, 7,112,210, 7,347,813, and 7,658,743, the entire disclosures of each of which is incorporated by reference. Some of these current methods of treating urinary stress incontinence by supporting the urethra employ tapes and meshes of artificial materials. In some instances, these artificial materials can cause complications and can be very difficult to remove completely requiring invasive surgery. With some of these current methods of treating urinary stress incontinence, it can be difficult for the physician to properly stabilize the urethral support, and/or adjust the support to the correct tension.

SUMMARY

This section provides a general summary of the disclosure, and is not a comprehensive disclosure of its full scope or all of its features.

Embodiments of the present invention provide an implantable device for treating a patient suffering from female urinary stress incontinence. In a preferred embodiment, the device comprises an elongate urethral stabilization sling for supporting the urethra. The sling has a central section and first and second lateral ends. First and second lateral self-fixating stabilization tissue engagement tabs extend from the first and second ends of the sling, respectively. These tabs are adapted for engaging supportive tissue superior to the portion of the urethra being supported by the urethral stabilization sling. Each tab preferably has a ratcheted section of alternating relatively projecting and relatively recessed portions for engaging and self-fixating into the supportive native tissue. These ratcheted sections are preferably configured to provide tactile and/or haptic feedback as the tab is pulled through the supporting native tissue, to facilitate proper tensioning and lateral stabilization of the urethral support sling.

The tabs are preferably made of an absorbable substance—one that is absorbed or otherwise dissolves in the body, reducing the amount for foreign material that is left in the body. By the time that the have dissolved, scar tissue will have formed to fix and secure the urethral stabilization support sling in the proper position under the urethra.

In some preferred embodiments of the invention some or all of the ratcheted portions of each tab can be formed by recesses on the tabs. In other preferred embodiments of the invention some or all of the ratcheted portions of each tab can be formed by projections or protuberances on the tab. In one particularly preferred embodiment the ratcheted portions of each tab are formed by braided section of multiple filaments forming alternating relatively projecting and relatively recessed portions projections on the tab.

In some alternative embodiments, the alternating relatively projecting and relatively recessed portions are substantially equally sized along the length of the self-fixating ratcheted tab portion. While in other alternative embodiments, some of the projections, some of the recesses, or both are sized differently from others of the projections and/or recesses.

In some alternative embodiments, the alternating relatively projecting and relatively recessed portions are substantially equally spaced along the length of the self-fixating tab ratcheted portion. While in other alternative embodiments, some of the tab projections, some of the recesses, or both are spaced differently from others of the projections and/or recesses.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Figure 7:
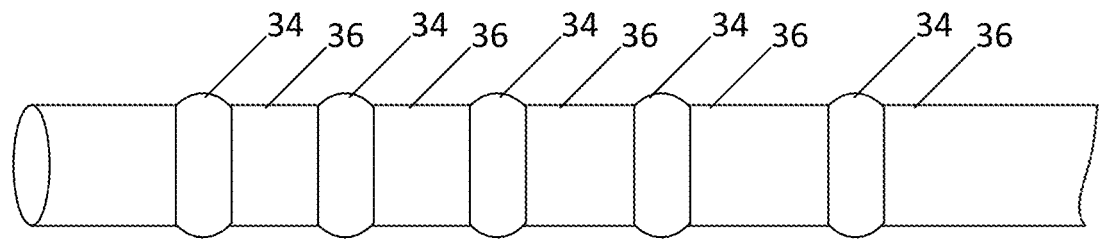
Figure 8:
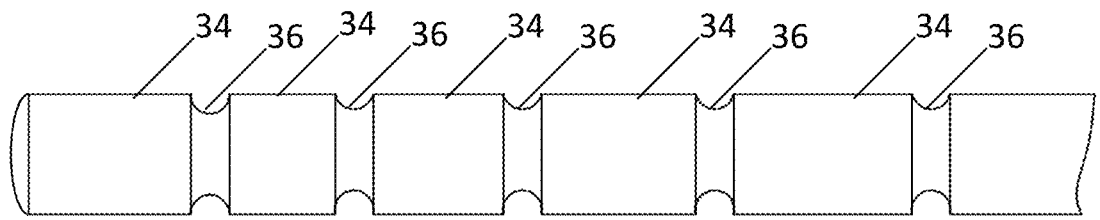

FIG. 7 is an enlarged perspective view of a fifth alternate construction of one of the tabs-of the implantable device of FIG. 1, showing some of the tab projections spaced further from adjacent projections than other of the projections; and FIG. 8 is an enlarged perspective view of a sixth alternate construction of one of the tabs of the implantable device of FIG. 1, showing some of the recesses spaced further from adjacent recesses than other of the recesses.

Figure 9:
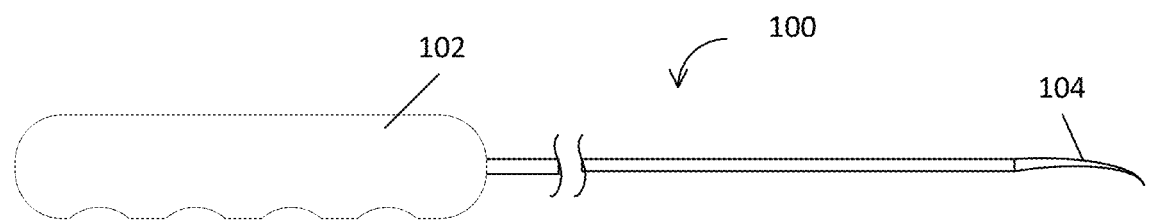

FIG. 9 is a side elevation view of a dilator that can be used to enlarge the openings formed in the abdominal wall to facilitate the placement of the implantable device.

Corresponding reference numerals indicate corresponding parts throughout the several views of the drawings.

DETAILED DESCRIPTION

Example embodiments will now be described more fully with reference to the accompanying drawings.

Embodiments of the present invention provide an implantable device for treating a patient suffering from female urinary stress incontinence. A preferred embodiment of such a device in indicated generally as 20 in FIG. 1. The device comprises an elongate central urethral stabilization sling 22 for supporting the urethra. The sling 22 has first and second ends 24 and 26. First and second tabs 28 and 30 extend from the first and second ends 24 and 26 of the sling 22, respectively. These self-fixating stabilization tissue engagement tabs 28 and 30 are adapted for engaging supportive tissue superior to the portion of the urethra being supported by the sling 22. Each of these tabs 28, 30 preferably has a ratcheted section 32 of alternating relatively projecting portions 34 and relatively recessed portions 36 for engaging the supportive native tissue in which the tabs are embedded.

These ratcheted sections 32 are preferably formed from braided or knotted strands, which provide an external configuration with projections and recesses. Alternatively, these ratcheted sections can be formed by forming protuberances or projections on the surface of the tabs, by forming recesses in the surface of the tabs, or by forming both protuberances and recesses in the surface of the tabs.

These ratcheted sections 32 are preferably also configured to provide tactile and/or haptic feedback as the tabs 28, 30 are pulled through the supporting tissue, to facilitate proper tensioning of the central urethral stabilization sling 22.

The central sling 22 can be made of a strip of a mesh of a polymeric material such as polypropylene or a combination of synthetic/absorbable composite or other suitable biocompatible material. The central sling could also be made from a strip of human cadaver or animal tissue, or it could even be autologous tissue harvested from the patient. The sling 22 is preferably between about 2.75 inches and about 17.38 inches (about 7.0 cm and about 44.0 cm) long, and between about 0.3937 inches and about 0.7874 inches (about 1.0 cm and about 2.0 cm) wide.

The center portion of the sling 22 is preferably identified, for example with one or more notches 40 and 42 formed in the edges of the sling 22. This allows the physician to center the sling 22 under the urethra by sight or by touch. Alternatively, the center portion can be identified by a colored stripes extending along the edges of the sling, or transversely across the sling), by other tactile elements formed on the sling, or any other suitable means.

The sling 22 preferably has one or more of anchoring barbs 44 on its underside, adjacent each end 24, 26. These anchoring barbs 44 can engage the surrounding tissue such as the urogenital diaphragm to help stabilize and secure the sling 22. In addition, or instead of these anchoring barbs, one or more suture holes 46 can be provided so that the physician can suture the sling to supporting tissue such as the urogenital diaphragm.

The tabs 28, 30 are preferably made of an absorbable substance—one that is absorbed or otherwise dissolves in the body, reducing the amount for foreign material that is left in the body. Any suitable absorbable material can be used for this purpose including catgut, or more preferably by synthetic absorbable polymers such as Vicryl, polydioxanone, polyglycolic acid, polylactic acid, polydioxanone, and caprolactone. By the time that the tabs 28, 30 have dissolved, scar tissue will have formed to secure the central and extending ends 24, 26 of the sling 22 in the proper position.

Figure 2:
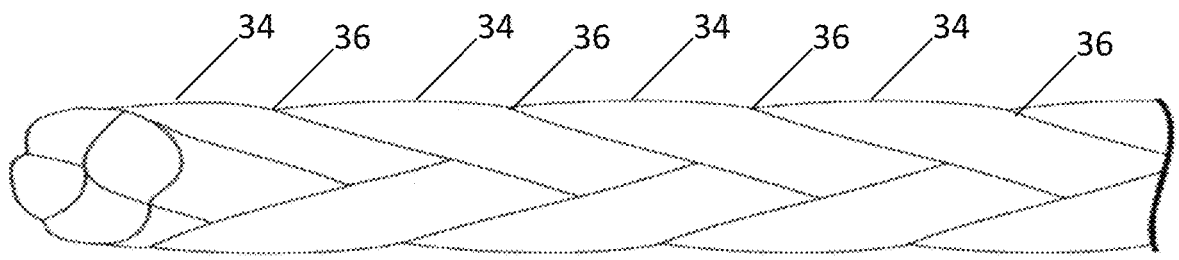
FIG. 2 is an enlarged perspective view of one of the tabs of the implantable device of FIG. 1 made from a braided material.

As shown in FIG. 2, in a preferred embodiment of the invention the tabs 28, 30 comprise braided material, such as a braided, absorbable suture material, the braiding forms the ratcheted section 32 of alternating relatively projecting portions 34 and relatively recessed portions 36 for engaging the supportive tissue in which the tab is embedded. As the tabs are pulled through the supportive native tissues, the projecting portions 34 and/or the recessed portions 36 engage and release the tissue. The projecting portions and/or recesses can engage and release the tissue as they pass through the tissue providing a haptic-indication of movement, allowing the physician to better gauge the movement of the tabs and achieve the proper tensioning of the sling engaging the urethra. The physician can also feel the projections and recesses and receive tactile feedback of the position and tension of the sling, and also determine whether the sling is evenly supported.

Figure 4:
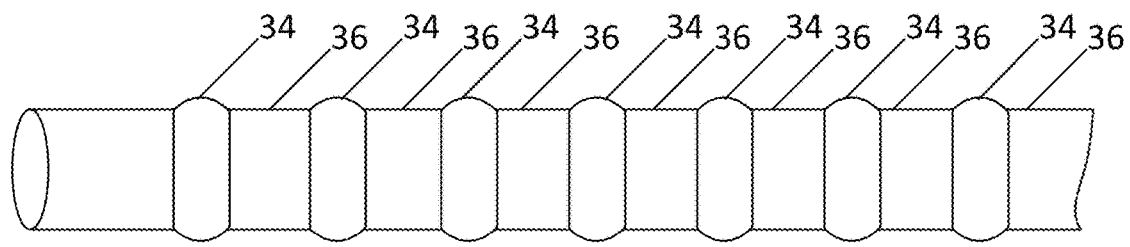
FIG. 4 is an enlarged perspective view of a second alternate construction of one of the tabs of the implantable device of FIG. 1, showing the ratcheted portions of the tabs being formed of projections (raised rings) from the surface of the tabs.
Figure 3:
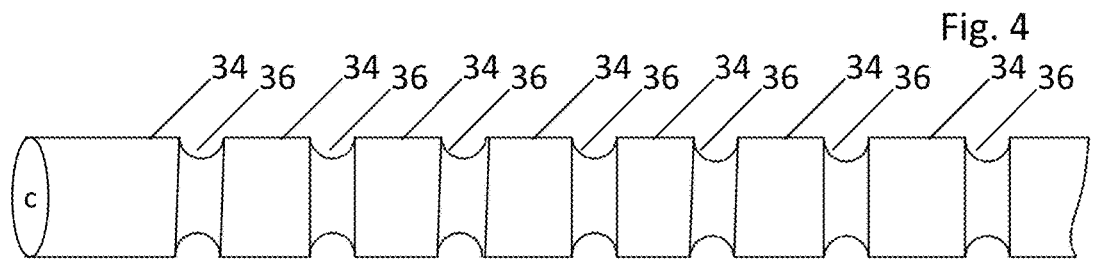
FIG. 3 is an enlarged side elevation view a first alternate construction of one of the tabs of the implantable device of FIG. 1, showing the self-fixating ratcheted tabs being formed with recesses (circular groove) in the surface of the tabs.

As shown in FIG. 3, in a first alternate construction some or all of the ratcheted portions 32 of each of the tabs 28 and 30 can be formed by recesses 36 on the tabs, with the projections 34 formed by the non-recessed portions of the surface of the tabs. As shown in FIG. 4, in a second alternate construction some or all of the ratcheted portions 32 of each tab can be formed by projections or protuberances 34 on the tab, with the recesses 36 formed by the non-protruding portions of the surface of the tab.

As shown in FIGS. 3 and 4, the protuberances 34 and the recesses 36 can be of substantially the same size, shape, and spacing. However, in other embodiments the sizes, shapes, or spacing of the protuberances and the recesses can differ. As shown in FIG. 3, the recesses can be formed of circular groves extending entirely around the circumference of the tab, but alternatively the recesses could be formed only partly around the tab, or could be intermittent, rather than continuous. As shown in FIG. 4, the projections can be formed of circular rings extending entirely around the circumference of the tab, but alternatively the projections could be formed only partly around the tab, or could be intermittent, rather than continuous.

Figure 5:
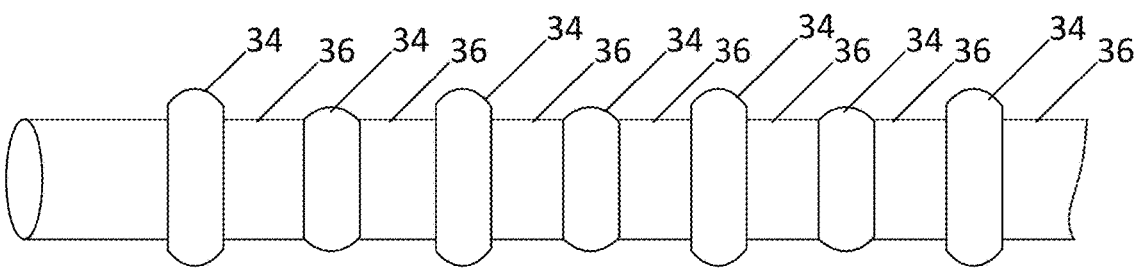
FIG. 5 is an enlarged perspective view of a third alternate construction of one of the tabs of the implantable device of FIG. 1, showing some of the projections projecting further than other of the projections.
Figure 6:
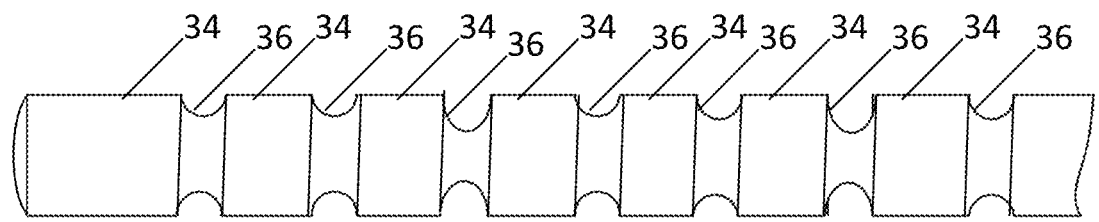
FIG. 6 is an enlarged perspective view of a fourth alternate construction of one of the tabs of the implantable device of FIG. 1, showing some of the recesses extending deeper than other of the recesses.

As shown in FIGS. 5 and 6, in a third and fourth alternate construction, the alternating relatively projecting and relatively recessed portions 34 and 36 are not equally sized along the length of the ratcheted portions 32 of each of the tabs 28 and 30. As shown in FIG. 5, every other projection 34 projects further than the other projections. This can be sensed haptically as the tab is pulled through the patient's tissue, and can be visually and tactically observed by the physician As shown in FIG. 6 every third recesses 36 is deeper than the other recesses 36. This can be sensed haptically as the tab is pulled through the patient's tissue, and can be visually and tactically observed by the physician.

As shown in FIGS. 7 and 8, in fifth and sixth alternate constructions, the alternating relatively projecting and relatively recessed portions can be variably spaced along the length of the ratcheted portions 32 of the tabs 24 and 26. As shown in FIG. 7, the spacing of the projections 34 (determined by the length of the recessed portions 36) increases toward one end of the tab. Alternatively some other spacing to could be provided, for example decreasing rather than increasing toward one end, or in changing in some repeating pattern. This can be sensed haptically as tab is pulled through the patient's tissue, and can be visually and tactically observed by the physician. As shown in FIG. 8, the spacing of the recesses 36 (determined by the length of the projecting portions 34) increases toward one end of the tab. Alternatively some other spacing to could be provided, for example decreasing rather than increasing toward one end, or in changing in some repeating pattern. This can be sensed haptically as tab is pulled through the patient's tissue, and can be visually and tactically observed by the physician.

Operation

In use, the implantable device 20 for treating a patient suffering from female urinary stress incontinence can be placed trans-vaginally and the elongate sling 22 positioned under the subject's urethra, with a tab on either side of the central urethral sling 22. Then each of the tabs 24, 26 can be inserted into supportive tissue superior to the supported portion of the urethra, with using curved elongate needles to penetrate the abdominal wall retropubically or suprapubically, so that the free ends of the tabs extend outside the subject's body. The physician can grasp each of these free ends, and pull to tension the central urethral sling 22 extending below the urethra. The ratcheted portion 32 of each tab helps engage the tab in the native tissue and abdominal wall. The ratcheted portion 32 can also provide a haptic, visual, and/or tactile cue to the physician about the movement and the position of the tabs and the sling that they are stabilizing 24 and 26. The various differences in sizing and spacing of the protuberances 34 and recesses 36 can enhance this effect, as well as improve the engagement of the tabs with the supportive native tissue. Once the desired tension is achieved in the central sling 22, the tabs 24 and 26 can be either tied together, or simply cut off leaving a portion embedded in the abdomen wall to provide support for the central sling until tissue ingrowth has occurred.

A dilator, such as dilator 100 in FIG. 9 can be used to enlarge the openings formed in the abdominal wall to facilitate the passage of the tabs and the ends of the sheath. As shown in FIG. 9, the dilator 100 has a handle 102 and a tapering pointed tip 104. The tip is preferably 2-4 cm long and tapers in a smooth continuous manner from a cross sectional diameter of about 1.5 cm to 0 at the distal tip. The tip 104 can curve along its longitudinal access to facilitate manipulation in the surgical space. The dilator 100 can be inserted into a puncture opening, and widen each opening to facilitate the passage of the anchor and the end of the sling into each opening.

The tabs are preferably dissolvable so that over time they are absorbed by the body leaving only the central sling 22, which is held in place by scar tissue that forms before the tabs are dissolved. Even when an artificial (e.g. polymer mesh) is used for the central sling, the use of dissolvable tabs minimizes the amount of foreign material that is left in the body long term, reducing the opportunity for complications.

Figure 1A:
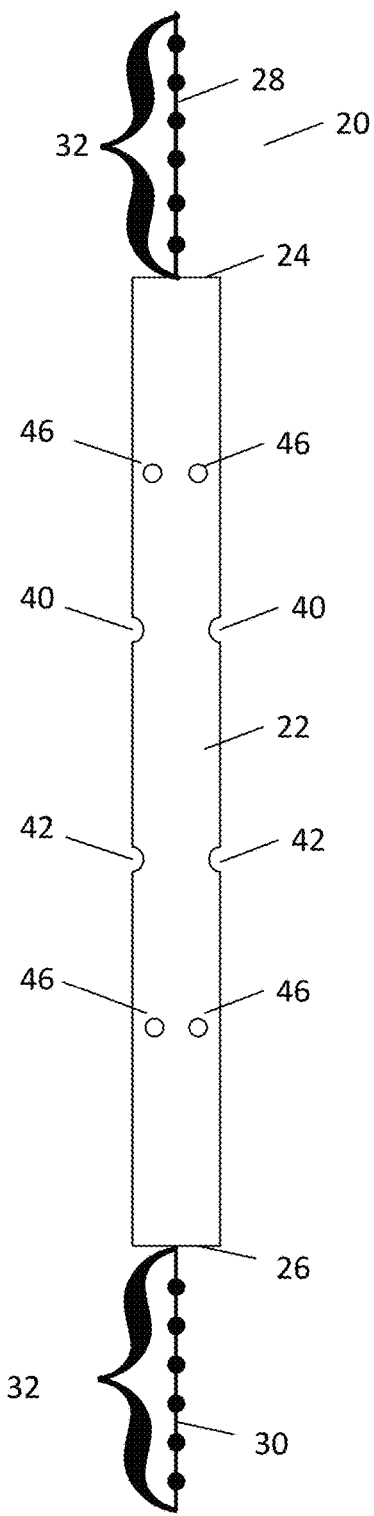
FIG. 1A is a top plan view of an implantable device for treating a patient suffering from female urinary stress incontinence according to a first preferred embodiment of this invention.
Figure 1B:
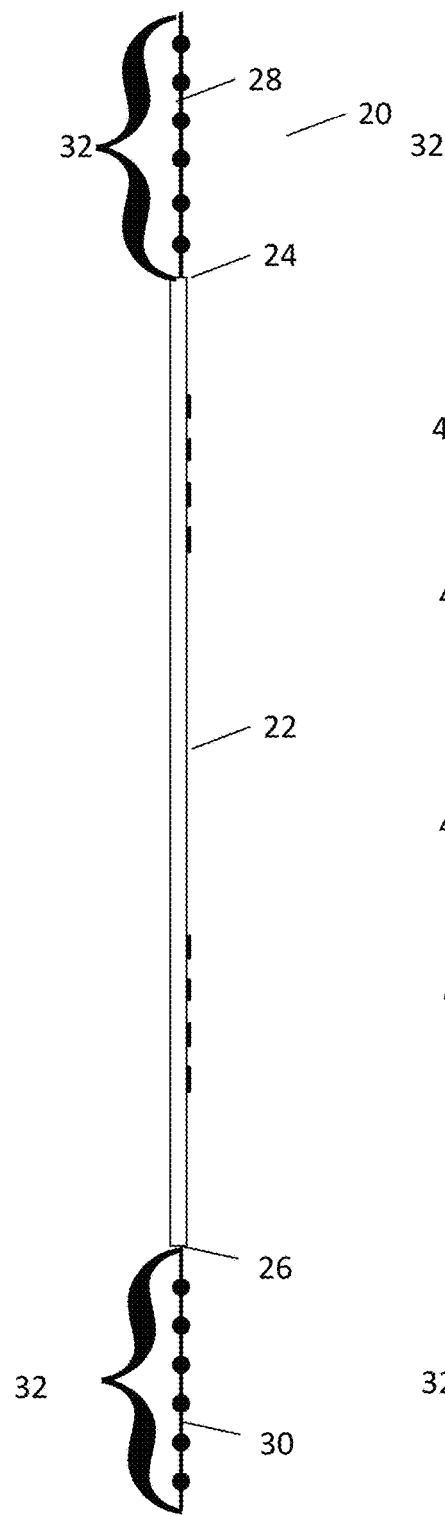
FIG. 1B is a side elevation view of the device of FIG. 1.
Figure 1C:
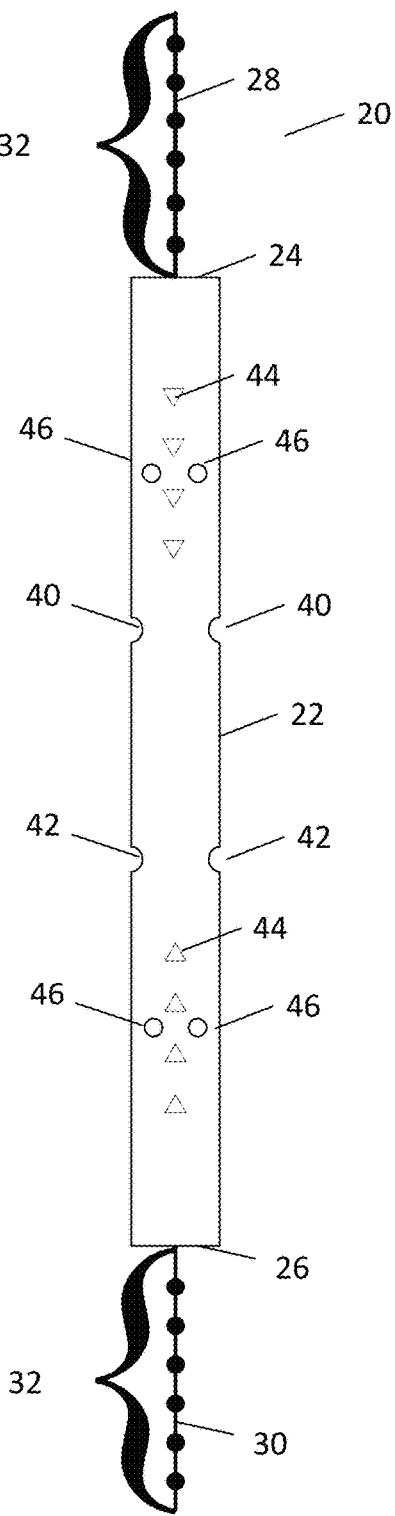
FIG. 1C is a bottom plan view of the device of FIG. 1.
Figure 1D:
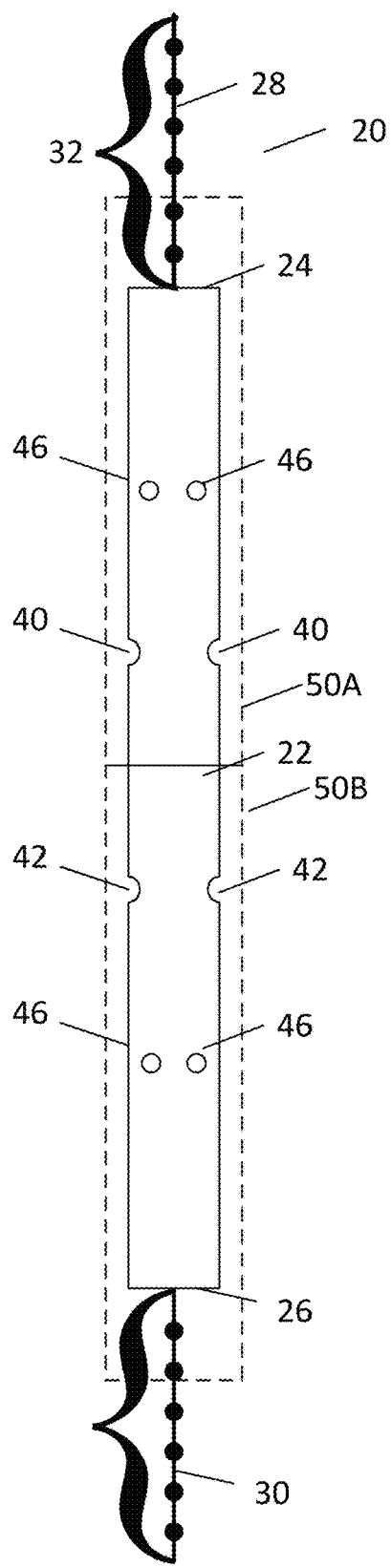
FIG. 1D is a top plan view of the device of FIG. 1, showing two removable protective sheaths mounted thereon.

As shown in FIG. 1D, the any of the embodiments of the device can be provided with one or more removable protective sheaths for protecting the sling 22 during introduction of the sling into the body and placement. Two such sheaths 50A and 50B are shown in FIG. 1D, although there could be a single sheath if desired. After the sling is introduced into the body, the sheaths 50A and 50B can be removed by sliding them off over their respective ends of the sling. Alternatively the slings 50A and 50B can have an have a longitudinally extending slit formed by overlapping edges of the sheath material, through which the sheath can be removed from around the sling. In still another alternative the sheath can be a simple thin-walled tube that can be cut from around the sheath.

Figure 1E:
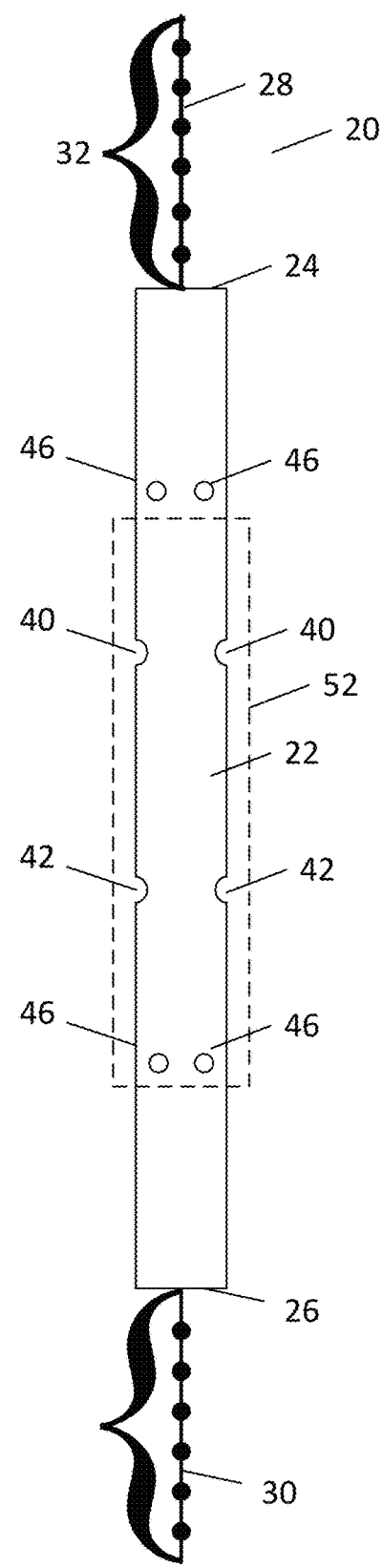
FIG. 1E is a top plan view of the device of FIG. 1, showing a centering jig mounted thereon.

As shown in FIG. 1E in addition to, or instead of a protective sheath like sheaths 50A and 50B, a centering jig 52 can be provided around the center portion of the sling. The jig 52 preferably has a length of between about 1.0 cm and about 4.0 cm, and more preferably between about 1.5 cm and 2.7 cm, and most preferably between about 1.2 cm and about 1.7 cm. The ends of the jig 52 are each spaced the same distance from are preferably equally spaced from the center of the sling. The jig 52 preferably remains during the entire installation process, and allows the physician to center the device under the urethra, pulling on the tab on each side until the ends of the jig 52 are each spaced the same distance from the interior wall, and the jig is in contact with the urethra, thereby centering the sling. For example, the sling can be tensioned until each end of the jig contacts the abdominal wall, or until each end of the jig is spaced 2 cm from the abdominal wall. Once the sling is placed, the physician can remove the jig, which preferably has a longitudinally extending slot for this purpose. Alternatively, the physician can cut the jig 52 from the sling. After the jig is removed from the sling, the physician can adjust the tension by pulling on the anchors, being careful to adjust each end so that the sheath remains generally centered relative to the urethra.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. An implantable device for treating a patient suffering from female urinary stress incontinence, comprising:
   an elongate central sling for supporting the urethra, the central sling having first and second ends: first and second self-fixating stabilization tissue engagement tabs extending from the first and second ends of the central sling, respectively configured for extending through and engaging supportive tissue superior to a portion of a urethra being supported, each of the tabs having ratcheted sections of alternating relatively projecting and relatively recessed portions for engaging the supportive tissue, the ratcheted sections of the tabs being sized and configured to provide haptic, visual or tactile feedback as each tab is pulled through the supportive tissue.

2. The implantable device according to claim 1 wherein the tabs are dissolvable.

3. The implantable device according to claim 1 wherein at least a portion of each tab is dissolvable.

4. The implantable device according to claim 1 wherein the ratcheted sections of each tab are formed by recesses on the tab.

5. The implantable device according to claim 1 wherein the ratcheted sections of each tab are formed by projections on the tab.

6. The implantable device according to claim 1 wherein the ratcheted sections of each tab are formed by a braided section of multiple filaments forming alternating relatively projecting and relatively recessed portions.

7. The implantable device according to claim 6 wherein the alternating relatively projecting and relatively recessed portions are substantially equally sized.

8. The implantable device according to claim 7 wherein the alternating relatively projecting and relatively recessed portions are substantially equally spaced.

9. The implantable device according to claim 1 wherein the alternating relatively projecting and relatively recessed portions are substantially equally spaced.

10. The implantable device according to claim 1 further comprising at least one removable sheath disposed over a portion of the device to protect the device while the device is being introduced into a subject.

11. The implantable device according to claim 10 wherein there are at least two removable sheaths disposed over portions of the device.

12. The implantable device according to claim 1 further comprising a removable jig disposed over a central portion of the sling, the jig having first and second ends indicating equal distances from the center of the sling.

13. A method of implanting a sling in a body to support the urethra, comprising:
   introducing an elongate central sling for supporting a urethra into an abdominal cavity, the central sling having first and second ends and first and second self-fixating stabilization tissue engagement tabs extending from the first and second ends of the central sling, respectively for engaging supportive tissue superior to a portion of the urethra being supported, each of the tabs having ratcheted sections of alternating relatively projecting and relatively recessed portions for engaging the supportive tissue, the ratcheted sections of the tabs being sized and configured to provide haptic, visual or tactile feedback as each tab is pulled through the supportive tissue;
   forming two passages through the abdominal wall on opposite sides of the urethra; and
   anchoring one of the first and second tabs in each of the passages, and pulling on the tabs to tension the sling using feedback from the ratcheted sections to maintain a proper position of the sling.

14. The method according to claim 13 wherein the sling has a removable jig having first and second ends, and wherein the step of pulling on the tabs to tension the sling, includes pulling on the tabs until the jig contacts the urethra and the ends of the jig are each spaced the same distance from the abdominal wall, and then removing the jig from the sling.

* * * * *